US012727963B2

(12) United States Patent
Hoegerle et al.

(10) Patent No.: US 12,727,963 B2
(45) Date of Patent: Sep. 8, 2026

(54) INTEGRATED RFID TAG IN A MANUAL INSTRUMENT

(71) Applicant: Aesculap AG, Tuttlingen (DE)

(72) Inventors: Roland-Alois Hoegerle, Tuttlingen (DE); Frederick Lenzenhuber, Tuttlingen (DE); Ralf Pfister, Trossingen (DE); André Buerk, Villingen-Schwenningen (DE)

(73) Assignee: Aesculap AG, Tuttlingen (DE)

( * ) Notice: Subject to any disclaimer, the term of this patent is extended or adjusted under 35 U.S.C. 154(b) by 171 days.

(21) Appl. No.: 18/283,549

(22) PCT Filed: Mar. 23, 2022

(86) PCT No.: PCT/EP2022/057650
§ 371 (c)(1),
(2) Date: Sep. 22, 2023

(87) PCT Pub. No.: WO2022/200441
PCT Pub. Date: Sep. 29, 2022

(65) Prior Publication Data

US 2024/0164866 A1 May 23, 2024

(30) Foreign Application Priority Data

Mar. 24, 2021 (DE) .................... 10 2021 107 440.1

(51) Int. Cl.
*A61B 90/98* (2016.01)
*A61B 17/28* (2006.01)
(Continued)

(52) U.S. Cl.
CPC .......... *A61B 90/98* (2016.02); *A61B 17/2841* (2013.01); *A61B 17/3201* (2013.01);
(Continued)

(58) Field of Classification Search
CPC ................ A61B 90/98; A61B 17/2841; A61B 17/3201; A61B 17/28; A61B 2017/00438;
(Continued)

(56) References Cited

U.S. PATENT DOCUMENTS 7,837,694 B2 11/2010 Tethrake et al.
7,898,420 B2 3/2011 Blair et al.
(Continued)

FOREIGN PATENT DOCUMENTS

CN 108498188 A 9/2018
CN 211599193 U 9/2020
(Continued)

OTHER PUBLICATIONS

Search Report received in German Application No. 10 2021 107 440.1 dated Nov. 26, 2021, with translation, 13 pages.
(Continued)

*Primary Examiner* — Brooke Labranche
(74) *Attorney, Agent, or Firm* — Christopher A. Rothe; CM Law

(57) ABSTRACT

A medical manual instrument has an instrument body with at least one effector portion, at least one gripping portion and an RFID tag. The RFID tag is preferably a glass/ceramic tag housed in the instrument body in a recessed manner. A cut-out or an open section is formed in the instrument body in a region which is substantially force-free when actuating the manual instrument in an operation, in which cut-out or open section a separate recessed tag holder is housed. The holder fills the cut-out or the open section so as to be adapted to the shape of the manual instrument. The medical manual instrument can be part of a system that includes the medical manual instrument and a reader that can be coupled to the RFID tag for signal transmission.

16 Claims, 4 Drawing Sheets

(51) Int. Cl.
*A61B 17/3201* (2006.01)
*A61B 17/00* (2006.01)

(52) U.S. Cl.
CPC ............... *A61B 2017/00438* (2013.01); *A61B 2017/00477* (2013.01); *A61B 2017/00526* (2013.01)

(58) Field of Classification Search
CPC ........... A61B 2017/00477; A61B 2017/00526; A61B 2018/146
See application file for complete search history.

(56) References Cited

U.S. PATENT DOCUMENTS

| | | | | |
|---|---|---|---|---|
| 9,940,569 | B2 | 4/2018 | Lynch et al. | |
| 2006/0244652 | A1 | 11/2006 | Tethrake et al. | |
| 2008/0238677 | A1 | 10/2008 | Blair et al. | |
| 2009/0283595 | A1 | 11/2009 | White et al. | |
| 2010/0033309 | A1 | 2/2010 | Blair | |
| 2014/0088570 | A1* | 3/2014 | Sergeant ................ | A61B 90/92 606/1 |
| 2014/0131454 | A1* | 5/2014 | Weisshaupt ............ | A61B 90/98 235/492 |
| 2014/0263633 | A1 | 9/2014 | Schmucker et al. | |
| 2016/0128798 | A1 | 5/2016 | Bovet et al. | |
| 2017/0185884 | A1 | 6/2017 | Lynch et al. | |
| 2018/0098822 | A1 | 4/2018 | Bilsøe | |
| 2020/0170657 | A1 | 6/2020 | Blaesius et al. | |
| 2022/0257330 | A1 | 8/2022 | Hoegerle et al. | |
| 2022/0287797 | A1 | 9/2022 | Hoegerle et al. | |

FOREIGN PATENT DOCUMENTS

| | | | |
|---|---|---|---|
| DE | 102019122349 | A1 | 2/2021 |
| FR | 2957240 | A1 | 9/2011 |
| JP | 2019185494 | A | 10/2019 |
| WO | 2015076746 | A1 | 5/2015 |
| WO | 2015177538 | A1 | 11/2015 |
| WO | 2021005224 | A2 | 1/2021 |

OTHER PUBLICATIONS

Search Report received in International Application No. PCT/EP2022/057650 dated Aug. 1, 2022, with translation, 5 pages.

Written Opinion received in International Application No. PCT/EP2022/057650 dated Aug. 1, 2022, with translation, 12 pages.

Office Action received in Japanese Application No. 2023-558654 dated Aug. 29, 2025, with translation, 19 pages.

Office Action received in Chinese Application No. 202280024093.4 dated Jun. 30, 2026, with translation, 12 pages.

Office Action received in European Application No. 22 719 210.1-1113 dated Jul. 16, 2026, with translation, 14 pages.

Search Report received in Chinese Application No. 2022800240934 dated Jun. 29, 2026, with translation, 6 pages.

* cited by examiner

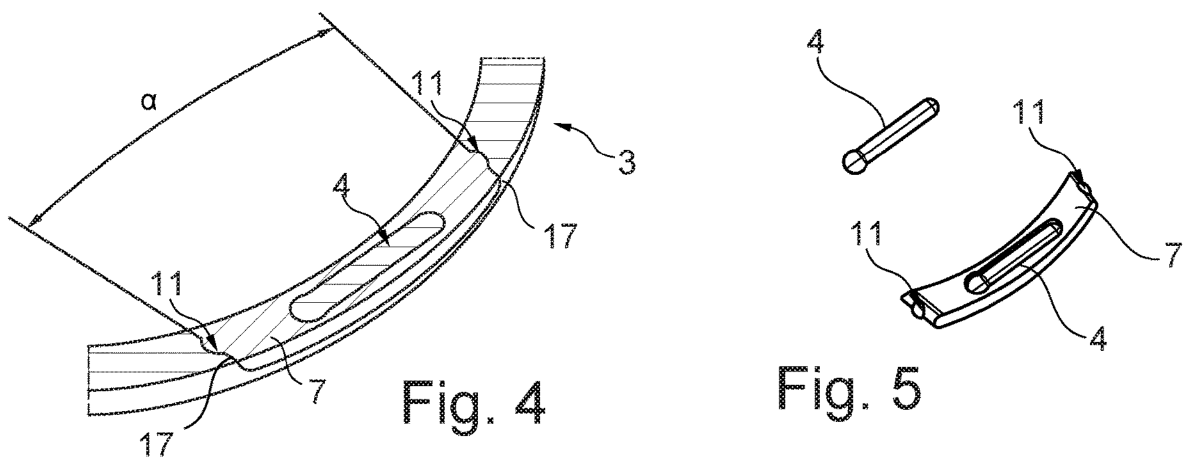
Fig. 4
Fig. 5
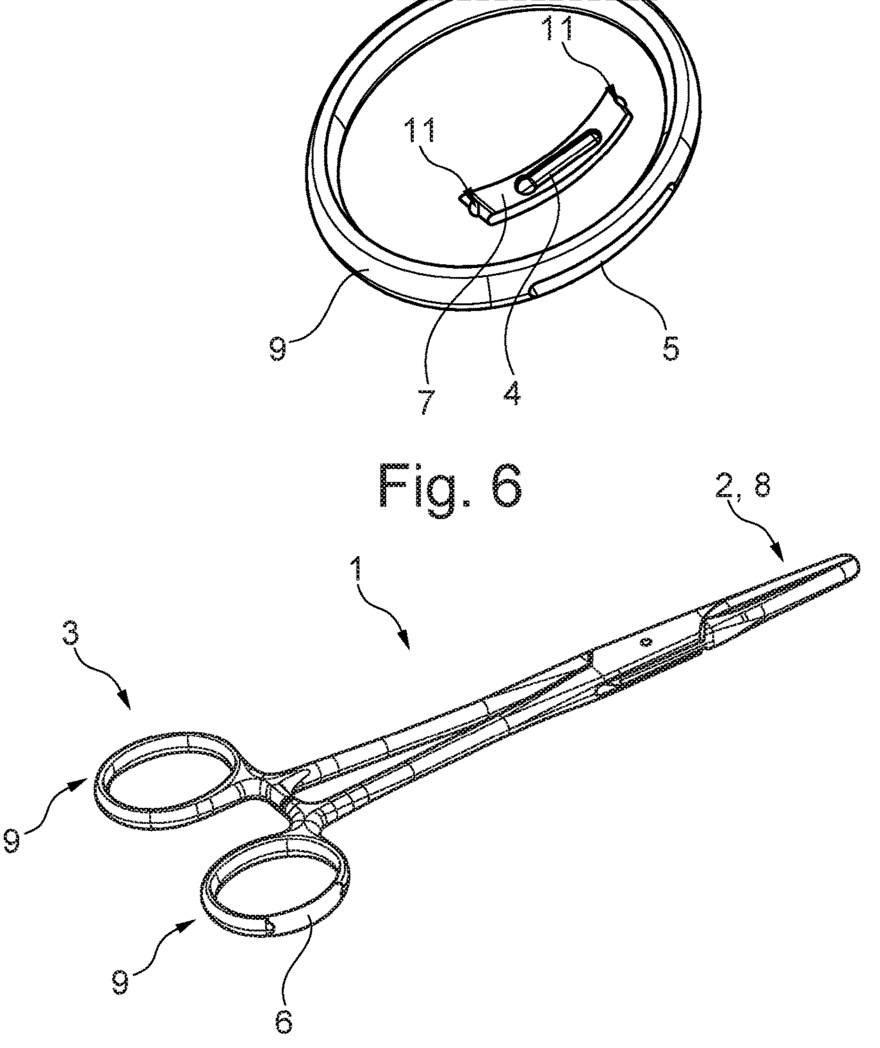
Fig. 6
Fig. 7

9
14
7

17
4
12
17
12
4
7

9
13
12
4
12
7

3
1
2
9
7, 14

INTEGRATED RFID TAG IN A MANUAL INSTRUMENT

CROSS-REFERENCE TO RELATED APPLICATIONS

This application is the United States national stage entry of International Application No. PCT/EP2022/057650, filed Mar. 23, 2022, and claims priority to German Application No. 10 2021 107 440.1, filed Mar. 24, 2021. The contents of International Application No. PCT/EP2022/057650 and German Application No. 10 2021 107 440.1 are incorporated by reference herein in their entireties.

FIELD

The present disclosure relates to a medical hand-held instrument with an instrument body having at least one gripping portion, at least one effector portion, and an RFID tag, which is preferably inserted as a glass/ceramic tag according to the subsurface principle in the instrument body.

BACKGROUND

Medical (marking) devices with RFID tags are already known. For example, U.S. Pat. No. 7,898,420 B2 discloses a transponder device and/or a housing for marking a surgical device, such as a metallic surgical instrument. The transponder device is provided to have a non-elastic, preferably non-metallic, rigid transponder housing attachable to a portion of the surgical instrument. The housing has a transponder receiving cavity that is distanced at least 1 millimeter, and preferably 2 millimeters, from any portion of the surgical device when the housing is attached to the surgical device. The housing may be removably attached to the surgical device or permanently attached. A transponder installed in the transponder receiving cavity is used.

EP 3 146 479 A1 describes an RFID tag assembly that has a passive RFID tag on metal and a mounting element. The passive RFID tag mounted on metal is arranged such that an RF signal is transmittable. The mounting element is made of an electrically conductive material and includes a base portion and at least one wall portion extending outward with respect to a first surface of the base portion. The at least one wall portion is configured to at least partially define a cut-out in which the RFID tag is connected up to the at least one wall portion. A surgical instrument to which an RFID tag assembly is attached is also provided.

Although such RFID tags are comparatively small components, the RFID tag assemblies/devices retrofitted in the prior art form additional attack surfaces for contamination and are also a hindrance when handling the surgical or medical instruments. Additionally applied RFID tags may form crevices and cracks (virus and bacteria nests) in which germs or the like can deposit, which is of course very disadvantageous in medicine. In addition, the retrofitted RFID tags may restrict the handling of the ergonomically shaped surgical instruments and, in the worst case, may form corners and edges where a surgeon's glove may be damaged on contact or may develop a hole/tear.

In principle, it is possible to place an RFID tag or a corresponding (marking) device at such a position on the corresponding medical instrument where the least possible negative influence on instrument handling can be expected. However, this massively restricts the variety of positioning options depending on the type of instrument, and deteriorations, for example in data transmission capability and the like, may have to be accepted.

Another disadvantage in the prior art is that passive RFID tags have to be placed at a short distance from a readout device due to their sometimes short transmission range. For this reason, it is often only possible in the prior art to apply the RFID tags subsequently to an outer surface of a surgical instrument in order to keep the distance between the RFID chip and the read out device as short as possible. For the reasons mentioned above, care must be taken to ensure that the outer surface provided for this purpose is located at an instrument site that has only a minor influence on instrument handling and still permits sufficient readout quality.

In this respect, there is growing interest in counting product-related processing cycles for products and in recording and documenting this information and using it to process relevant findings. Such a processing cycle includes manual pre-cleaning (with brushes), ultrasonic cleaning if necessary, cleaning in the WS (washer disinfector), oiling if necessary, and sterilization. Due to the increasingly important issues of tracking, tracing and lifecycle management in the future and the provision of evidence in the event of complaints, the following information on medical products is of importance:

- general condition
- service life/end
- maintenance interval
- performance and suitability for follow-up surgery (as described in the purpose statement).
- reduced maintenance of the product and possible product damage
- temperature overshoots/undershoots and possible product damage Up to now, it has not been possible to offer customers/users services adapted to their needs and individually tailored business models, if the disadvantages described at the beginning are to be avoided. It is therefore desirable to be able to see immediately how often a product has been reprocessed (correctly) and whether there are any deficits in the process or whether maintenance/repair is required. Currently, products have to be subjected to a defined (routine) maintenance interval, although this might not be necessary. In times of digitalization, it is therefore desirable to offer customers services that are individually and possibly variably adapted to them or to the instrument as well as individually adapted business models.

In particular, ring instruments such as scissors, forceps and similar hand-held instruments pose the problem of requiring time-consuming retrofitting of the products with RFID tags, for example. In the prior art, the RFID chips/tags have to be encapsulated or pressed into the handpieces/hand-held instruments or applied by ultrasonic welding. Alternatively, UHF tags are often described in the prior art, although these make read-in/read-out more difficult, since tags in adjacent products could also be detected due to the read range, which does not serve the basic idea of individual, secure tracking of a single instrument. Even more problematic is when only the contents of a sieve/sieve basket are to be detected and products on the adjacent sieve/sieve basket are also detected.

In summary, however, an integrated assembly initially means material weakening on the hand-held instrument and an additive assembly means a change in the outer geometry of the hand-held instrument. Material weakening can basically be reduced by additional material reinforcement in the weakened region, by the integrated insert itself taking over the material weakening (bridging), or by selecting the position of the material weakening in such a way that it plays no role in the provided instrument insert. This can be achieved by the fact that the selected position already has a large material thickness, which is only slightly influenced by the integration of a tag.

It has become apparent, however, for the present application that not all medical hand-held instruments are suitable for retrofitting with an RFID tag according to the current procedure. Nevertheless, it is intended to be possible in principle to count the processing cycles for all products in combination with individualized storage and to save this information in the product itself, in particular to consider whether all individual process steps have been (correctly) observed and carried out.

SUMMARY

Thus, the object of the present invention is to provide a medical device or a medical/surgical instrument, in particular ring instruments, with an RFID tag that ensures good and safe handling both with regard to the instrument properties as such and to the data transmission properties of the RFID tag. A further object of the present invention is preferably to ensure good cleaning and/or sterilization of the device/medical instrument equipped therewith according to the invention. An additional object of the invention is further preferably to ensure reception enhancement of one and more RFID tags inserted/applied.

The core of the present invention substantially is that a cut-out or open section is configured in the instrument body in a region which is substantially force-free during operative activation of the hand-held instrument (e.g. closing movement of forceps/cutting movement of scissors etc.), wherein in the cut-out or open section, a separate subsurface tag holder (material bridge) is inserted, which fills the cut-out or open section in a form-adapted manner with respect to the hand-held instrument. Accordingly, the position of the material weakening is selected such that the position is not integrated into the force flow over which an operative activation force is directed.

In other words, it is preferred if the medical hand-held instrument is a ring instrument, such as (surgical) scissors, forceps or the like. Accordingly, alternatively, a medical ring instrument has an instrument body having at least one gripping portion, at least one effector portion and an RFID tag preferably inserted as a glass/ceramic tag according to the subsurface principle in the instrument body (integral assembly), wherein a cut-out or open section (indentation or material interruption) is configured in the instrument body in a region which is substantially force-free during operative activation of the hand-held instrument, wherein in the cut-out or open section, a separate subsurface tag holder (material bridge) is inserted, which fills the cut-out or open section in a form-adapted manner with respect to the hand-held instrument. This geometric modification and matching of the surrounding components increases reception, in particular the distance to the reading and writing device, of the RFID tag. With regard to medical hand-held instruments, in particular ring instruments, it is possible to accommodate a force absorption during operation and also to realize the principle of the slot antenna.

It is advantageous here that the reception and reliability, in particular the distance to the reading and writing device, of the RFID tag/chip can be significantly influenced by this geometric installation situation as well as the surrounding components. The RFID tag is preferably always installed under the surface (i.e. set back relative to the instrument surface) so that the RFID tag is positioned below the opening and does not protrude beyond it.

RFID tags can also be understood as NFC tags, which represent a sub-form of RFID technology. Thus, according to the invention, an NFC tag can also be used instead of an RFID tag. Further preferably, the RFID tag is an RFID transponder for storing information associated with a specific object (in this case the medical instrument). This so-called 'identifier' can be individualized according to the requirements of the particular process. Preferably, the RFID tag consists of:

- at least one microchip, preferably in the size around a few millimeters in diameter,
- at least one antenna, preferably in the form of a coil,
- at least one carrier or housing, the housing preferably being watertight and/or airtight and preferably protecting the transponder electronics from the environment,
- in case of an active RFID tag, additionally at least one energy source, preferably a battery/accumulator or a capacitor.

In case of passive transponders, the energy supply is provided externally via the antenna. Preferably, the RFID tag of the invention is a passive RFID tag. Preferably, the RFID tag also has a (rod-shaped) ferrite core with a coil wound around it.

The RFID tag is provided and adapted to store at least one of the following information or respectively is characterized by the following storage data:

- documenting information in the product (medical hand-held instrument/ring instrument)
- transparency in case of service (RFID tag carries the information)
- use determination,
- new business models (pay per use, etc.),
- indication of the service life (MDR requirement, standard requirement),
- improved reception of RFID tags in the products,
- almost no ergonomic modification of the product to maintain familiarity for the operator.

In other words, it is preferred that the RFID tag/chip used is a glass tag, which can be procured in different sizes. Other materials for enclosing the assembly are also conceivable. By optimizing the surrounding components, the reading and writing distance can be significantly influenced and the distance increased.

The geometry surrounding/encompassing the RFID tag/RFID pill/glass tag may be made of any material. However, there always has to be a gap parallel to the glass tag on the exterior of the product. The coil is located directly in the groove (subsurface). This opening can be either free or made of a signal-permeable material. The size varies in length and width to optimize the reading and writing distance.

It is advantageous if the at least one gripping portion has two branches, the at least one effector portion has two annularly tapering handles, and the cut-out or open section is arranged on a side of the at least one annularly tapering handle facing away from the other annularly tapering handle of the hand-held instrument. An increased amount of force is applied when the medical ring instrument is closed. When opening the ring instrument, a much lower force acts on the annularly tapering handle of the medical hand-held instrument. This provides an optimized way of installation to achieve reliability and signal amplification/reception. Since the subsurface tag holder is located on the outside of the annularly tapering handle in the direction away from the second handle, the subsurface tag holder is subjected to the lower force of reopening due to the arrangement. The geometry of the subsurface tag holder described below prevents it from being pushed out when a possibly increased force is applied. By optimizing the geometry of the subsurface tag holder (plastic part), the force can be absorbed much better and the plastic carrier/subsurface tag holder is prevented from escaping.

The subsurface tag holder is provided so that when an increased force is applied, the force flow causes the subsurface tag holder to bend/yield, but not to become detached. The choice of material, preferably plastic, is highly relevant here.

In other words, the medical device has the subsurface tag holder for at least one RFID tag integrated into the medical hand-held instrument or inserted within the medical hand-held instrument. This means that the subsurface tag holder according to the invention does not affect the normal (outer) shape of the medical hand-held instrument by a retrofitted RFID tag, but that the subsurface tag holder of the RFID tag is integrated or arranged below the/an outer surface of the medical hand-held instrument.

In yet other words, the subsurface tag holder is integrated/installed/configured/formed (hereinafter referred to as 'integrated') into the housing/shape/structure/body of the medical hand-held instrument (hereinafter referred to as 'body') or is integrated/inserted within the body of the medical hand-held instrument. The subsurface tag holder can be integrated as an individual/separate component (tag carrier), preferably in the form of a bridge or strip, into the body of the medical hand-held instrument (e.g. in a cut-out/notch or in an open section/material interruption) in the medical hand-held instrument whereby in this case the shape of the (signal-passage) opening forming on the surface of the instrument body can be essentially universal, since the separate subsurface tag holder is already equipped with the tag and the subsurface tag holder has been implemented/inserted into the cavity (the cut-out or the open section) of the medical hand-held instrument.

It is preferred if the subsurface tag holder is provided to receive the RFID tag therein in a positionally fixed manner, such that the RFID tag is recessed with respect to a surface of the at least one annularly tapering handle toward the interior of the subsurface tag holder. Preferably, in the present medical hand-held instrument, at least one RFID tag is inserted into the subsurface tag holder, and further preferably, the RFID tag has a cylindrical shape with rounded ends. The shape of the RFID tag is further preferably in pill form.

It is advantageous if the subsurface tag holder is provided and configured such that the RFID tag is exposed on the inside of the at least one handle toward the instrument environment. Further preferably, the subsurface tag holder has the shape of an elongated slot or groove adapted to receive the preferably cylindrical/pill-shaped RFID tag 'lying down', i.e. in the manner of a (flat) battery compartment.

Preferably, the RFID tag has an outer surface/housing made of a material that is permeable to radio frequencies and is further preferably waterproof and/or airtight. In other words, the housing of the RFID tag is made of a radio frequency/signal permeable material such as glass, ceramic, plastic, thermoplastic, duroplast, plastics in general and/or silicone, particularly preferably of a non-metallic material, with which the ferrite core is encapsulated together with the coils and chip wrapped around it.

In principle, the geometry and material of the medical hand-held instrument and the RFID tag, or its body, as well as the orientation of the subsurface tag holder with respect to the corresponding instrument surface are freely selectable. Preferably, however, a receptacle pocket for receiving the RFID tag in the subsurface tag holder is configured parallel to the RFID tag, in particular the coil of the RFID tag, such that the RFID tag aligns in its longitudinal direction parallel to the exterior of the body of the medical hand-held instrument (i.e., 'lying down'). The receptacle pocket may optionally remain free/open to the outside or may be filled/closed with a signal-permeable material.

In other words, the receptacle pocket can be provided with or without a cover made of the signal-permeable material. Finally, the RFID tag may already be shaped per se in the manner of a sealing cap in such a way that with insertion of the RFID tag into the receptacle pocket, the latter or its opening is sealed to the outside (waterproof/airproof) by the RFID tag itself.

If a signal-permeable core and/or socket is chosen as subsurface tag holder of the RFID tag/glass tag (e.g. thermoplastic, duroplast, plastics in general, silicone etc.), the reading and writing distance is optimized by a metal screen/reflector at least partially surrounding the carrier and spacing the RFID tag to a reading/read-out/writing device (hereinafter only referred to as reading device) with a geometrically defined opening in the region of the receptacle pocket in the separate subsurface tag holder. In other words, in one embodiment, the subsurface tag holder may be configured as a signal-permeable core (e.g., plastic) located in a medical hand-held instrument. The receptacle pocket in the subsurface tag holder is thereby provided and adapted to receive at least one RFID tag.

It is preferred if the subsurface tag holder is configured in such a way that it is form-fitted to the at least one handle via latch-behind hemispheres or projections on its short side and/or via anchor points on the upper side near the respective short side.

The short side of the subsurface tag holder corresponds to the contact surface between the subsurface tag holder and the (annular) handle of the medical hand-held instrument when the subsurface tag holder is inserted into the handle.

The latch-behind hemispheres or projections are preferably hemispherically configured projections which protrude in the longitudinal direction at the short side of the subsurface tag holder, i.e. toward the (annular) handle of the medical hand-held instrument, when the subsurface tag holder is inserted into the handle of the medical hand-held instrument.

In other words, it is preferred that the latch-behind hemispheres on the subsurface tag holder are provided to slide/engage into a respective bulge/hollow upon insertion of the subsurface tag holder into the handle of the medical ring instrument/hand-held instrument. The bulge is configured to receive the latch-behind hemispheres of the subsurface tag holder.

It is advantageous if the short sides of the subsurface tag holder each have a protruding latch-behind hemisphere or projection and the short sides are configured at a conical angle $\alpha$ to each other in order to insert and/or push the subsurface tag holder into the cut-out from the inside of the at least one handle in the direction toward the outside, so that the respective protruding latch-behind hemisphere engages in a respective milled recess/bulge of the at least one handle provided and adapted accordingly for this purpose.

The anchor points are projections projecting in the upward direction perpendicular to the RFID tag inserted in the subsurface tag holder, which are configured near the short side defined above to be received in annular receptacles of the handle of the medical hand-held instrument.

The annular receptacles are provided on the short side of the open section on the handle of the medical hand-held instrument. The annular receptacles are configured approximately halfway up or centered perpendicular to the contact surface or short side of the handle of the medical hand-held instrument. The annular receptacles do not extend over the entire height of the contact surface or of the short side of the handle of the medical hand-held instrument and have continuous bores in the direction parallel to the contact surface, which are provided to receive the anchor points of the subsurface tag holder.

It is advantageous if the upper side (the side into which the RFID tag is insertable) of the subsurface tag holder has a respective protruding anchor point which is provided and configured in each case, in order to insert and/or push the subsurface tag holder into the open section from an underside of the at least one handle in the direction of the upper side, so that the respective protruding anchor point can be pushed and/or inserted into a correspondingly provided and adapted annular receptacle/milled recess of the at least one handle.

It is preferred if an attachable cover is provided and configured for the subsurface tag holder inserted in the at least one handle, which can preferably be connected to the subsurface tag holder via adhesive bonding or ultrasonic welding. The cover is attached to the subsurface tag holder in the opposite direction to the insertion direction of the subsurface tag holder, so that the subsurface tag holder and the cover approximately continue the shape of the annularly tapering handle of the original shape.

It is advantageous if the subsurface tag holder is a plastic injection molded part which is provided and configured to be adapted to the inside and preferably the outside of the annular shape of the at least one handle.

In other words, it is provided that the open section or the cut-out is filled by the subsurface tag holder or the subsurface tag holder in combination with the cover in such a way that the shape of the annularly tapering handle is almost continued by the subsurface tag holder or the subsurface tag holder with the cover.

It is preferred that the subsurface tag holder with the anchor points is configured to accommodate larger RFID tags compared to the subsurface tag holder with the latch-behind hemispheres. The use of a larger RFID tag again has the advantage of providing a maximum achievable reading/writing distance without significantly altering the external shape of the medical hand-held instrument/ring instrument.

Furthermore, the present invention relates to a system comprising a medical hand-held instrument, in particular a ring instrument, comprising a reading device signal-coupleable with the RFID tag and configured with or as an instrument holder which is provided and adapted to hold or temporarily fix the medical hand-held instrument in a predetermined position and/or orientation relative to the reading device, in which signal transmission between RFID tag and reading device is enabled and preferably a plurality of RFID tags are simultaneously and securely readable.

In other words, the positioning of the RFID tag is optimal for inserting the instruments perpendicularly in the corresponding holders, ensuring the immediate proximity to the readout antenna and being able to read out a large number of (hand-held) instruments simultaneously and reliably (100% hit rate). For example, 50 instruments in the sieve basket can be read out simultaneously. The present invention is not exclusively limited to 50 instruments.

With this solution, the RFID tag is optimally protected against mechanical influences. In combination with the very high chemical and thermal resistance of the RFID tag, this solution is therefore suitable for a very high number of processing cycles (preferably >500 cycles). Furthermore, it is easily possible to read out individual instruments quickly and securely with a smartphone (e.g. for service purposes or similar).

In summary, the above aspects have the advantage of counting the processing cycles for all products in combination with individualized storage and of securing this information in the product itself. In particular, checking whether all individual processing steps have been observed and carried out. The number of processing cycles is a proportional measure to:

- general condition
- service life/end
- maintenance interval
- performance and suitability for follow-up surgery (as described in the purpose statement)
- reduced maintenance of the product and possible product damage
- temperature overshoots/undershoots and possible product damage Furthermore, the position of the RFID chips is relevant to the solution in conjunction with the smart tray to ensure that a plurality of RFID tags can also be read simultaneously. Therefore, the present invention comprises a reception enhancement of the RFID tags inserted into the medical hand-held instrument. Furthermore, the present invention comprises the idea of fitting RFID tags into medical ring instruments with high force absorption capacity to avoid accidental detachment.

BRIEF DESCRIPTION OF THE DRAWINGS

The invention is explained in more detail below via preferred embodiments with reference to the accompanying Figures.

FIG. 4 is a cross-sectional view of the handle of the ring instrument with an inserted subsurface tag holder in accordance with the first embodiment;

FIG. 5 is a diagram illustrating the subsurface tag holder and the RFID tag in accordance with the first embodiment;

FIG. 6 is a diagram illustrating the handle of the ring instrument, the subsurface tag holder and the RFID tag in accordance with the first embodiment;

FIG. 7 is a diagram illustrating a ring instrument according to the invention in accordance with a second embodiment;

DETAILED DESCRIPTION

Configuration examples of the present disclosure are described below based on the accompanying Figures.

Figure 1:
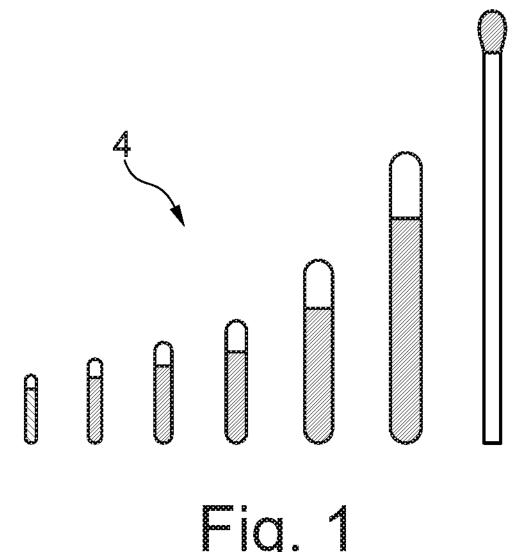
FIG. 1 is a diagram illustrating RFID tags that can be used according to the invention, in accordance with a first embodiment.

FIG. 1 is a diagram illustrating RFID tags 4 that can be used according to the invention. Various sizes of RFID tags 4 are shown, in particular so-called glass RFID tags, next to a commercially available match. Accordingly, the RFID tags 4 have a cylindrical shape with rounded ends resembling a shape of a rod or pill. Such RFID tags 4 are essentially prior art and therefore require no further description. Such an RFID tag 4 has a coil that is wound centrally around a rod-shaped ferrite core and is in contact with an RFID chip. The RFID chip is usually placed at one axial end of the ferrite core. This construction, consisting of the ferrite core, the coil 4 which surrounds it in sections, and the RFID chip arranged at the axial end, is enclosed by a radio wave-permeable material, e.g. a glass material, which forms the housing of the RFID tag 4. It is preferred if the assembly is encapsulated internally.

First Embodiment

Figure 2:
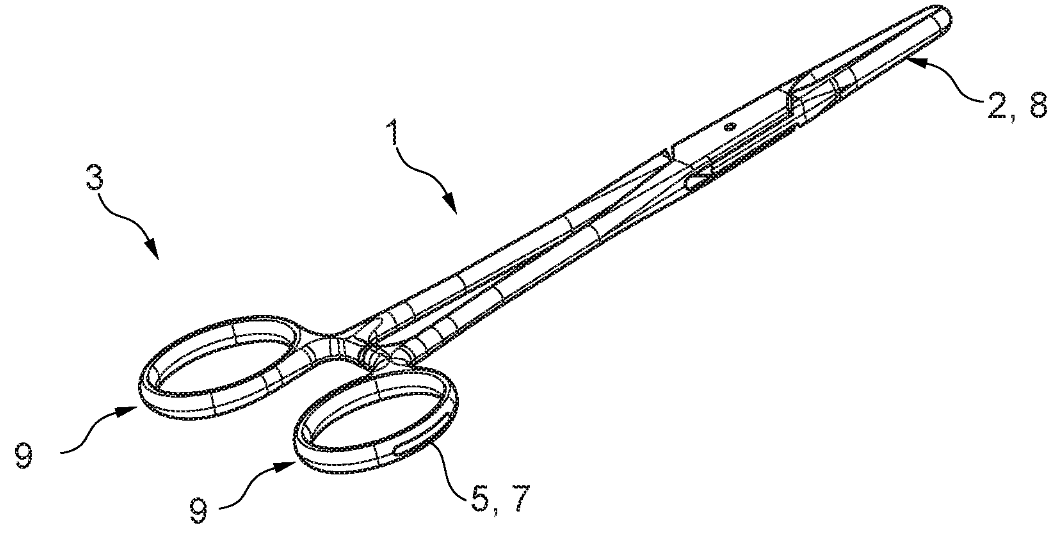
FIG. 2 is a diagram illustrating a ring instrument according to the invention in accordance with the first embodiment.

FIG. 2 is a diagram illustrating a ring instrument 1 according to the invention in accordance with the first embodiment. The medical hand-held instrument, in particular ring instrument 1 has an instrument body which comprises at least one effector portion 2 and at least one gripping/actuation portion 3. A cut-out 5 is provided in the at least one gripping portion 3.

The cut-out 5 is located in the gripping/ring portion 3 in a region that is essentially force-free during operative activation of the hand-held instrument/ring instrument 1. In the present example, a separate, bridge-like subsurface tag holder 7 gets/is inserted into the cut-out 5, having an RFID tag 4 that is inserted into the holder 7 according to the subsurface principle. The subsurface tag holder 7 fills the cut-out 5 in a manner adapted to the shape of the hand-held instrument/ring instrument 1 (so that a smooth/gap-free handle surface is created).

The at least one effector portion 2 has two effector branches 8 and the at least one gripping portion 3 has two annularly tapering handles 9. In this respect, the branches and handles form scissors of conventional construction. The cut-out 5 is arranged on a side of the at least one annularly tapering handle 9 facing away from the other annularly tapering handle 9 of the hand-held instrument/ring instrument 1.

Figure 3:
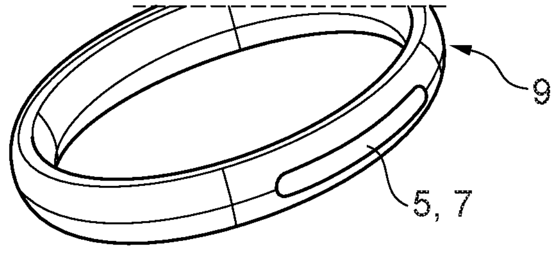
FIG. 3 is a diagram illustrating a handle of the ring instrument in accordance with the first embodiment.

FIG. 3 is a diagram illustrating an (annular) handle 9 of the hand-held instrument/ring instrument 1 in accordance with the first embodiment. In FIG. 3, one of the handles 9 of the hand-held instrument/ring instrument 1 according to FIG. 2 is shown enlarged. The cut-out 5 in the holder 7 is formed in a circumferential direction of the annularly tapering handle 9. Furthermore, the cut-out 5 is configured as a continuous slit from the inner side of the annularly tapering handle 9 through to the outer side of the annularly tapering handle 9. The cut-out 5 is centered as seen in the thickness direction and preferably extends in the circumferential direction over less than a quarter but more than an eighth of the entire annularly tapering handle 9.

FIG. 4 is a cross-sectional view of the handle 9 of the hand-held instrument/ring instrument 1 with an inserted subsurface tag holder 7 in accordance with the first embodiment. FIG. 5 is a view illustrating the subsurface tag holder 7 and the RFID tag 4 according to the first embodiment and FIG. 6 is a view illustrating the handle 9 of the hand-held instrument/ring instrument 1, the subsurface tag holder 7 and the RFID tag 4 in accordance with the first embodiment.

The subsurface tag holder 7 is provided to hold the RFID tag 4 in a positionally fixed manner. The RFID tag 4 is recessed with respect to a surface of the at least one annularly tapering handle 9 toward the interior of the subsurface tag holder 7. The subsurface tag holder 7 is configured such that the RFID tag 4 is exposed to the instrument environment on the inside of the at least one handle 9, as shown in both FIG. 5 and FIG. 6.

FIG. 4 shows that the subsurface tag holder 7 has a shape adapted to the annularly tapering handle 9. In particular, the annular handle 9 has a cut-out 5 at its ring portion facing away from the instrument, the cut-out 5 not being continuous in the thickness direction of the handle, so that a residual ring web remains and is filled by the holder 7 in a tile-like manner. Furthermore, the subsurface tag holder 7 is configured in such a way that it can be (non-detachably) fastened to the at least one handle 9 on its short side 17 (tile end portions/ends) via latch-behind hemispheres/projections 11 projecting in the longitudinal direction of the tile, for which purpose corresponding recesses/bores are configured on the handle ring on the respective end faces of the handle ring created as a result of the cut-out. Alternatively, it is also conceivable that the subsurface tag holder 7 is detachably inserted.

Furthermore, the short (front) sides 17 of the holder 7, which correspond to the contact surfaces between the subsurface tag holder 7 and the handle 9, preferably each have a protruding latch-behind hemisphere 11. Furthermore, the short sides 17 are configured at a (conical/acute) angle $\alpha$ to each other in order to insert and/or press/push the subsurface tag holder 7 from the inside of the at least one handle 9 toward the outside into the cut-out/interruption 5. In this way, the respective protruding latch-behind hemisphere 11 engages in a correspondingly provided and adapted milled recess/hollow/bore of the at least one handle 9.

Due to the conical/acute angle $\alpha$ between the two short sides 17 as well as the engaging latch-behind hemispheres 11, a manually applied force during opening the hand-held instrument/ring instrument 1 does not cause the subsurface tag holder 7 to be pushed through/outward to the outside of the handle 9.

Furthermore, it can be seen in FIG. 4 that the subsurface tag holder 7 can be inserted precisely into the cut-out/longitudinal notch 5 and thus completely fills it. Accordingly, the cut-out of the annularly tapering handle 9 is also configured with the conical angle $\alpha$ to prevent the inserted subsurface tag holder 7 from being pushed through.

According to the first embodiment, the original shape of the annularly tapering handle 9 remains unchanged.

Second Embodiment

FIG. 7 is a diagram illustrating a hand-held instrument/ring instrument 1 according to the invention in accordance with a second embodiment. The medical hand-held instrument, in particular ring instrument 1 has an instrument body which comprises at least one effector portion 2 and at least one gripping portion 3. In the at least one gripping portion 3, an open section is provided, in this case in the form of a continuous indentation 6. In particular, the annular handle 9 has a (complete) interruption 6 at its ring portion facing away from the instrument, which is filled by the holder 7 in a bridge-like manner.

The open section 6 is thus located in the gripping portion 3 in a region that is essentially force-free during operative activation of the hand-held instrument/ring instrument 1. A separate subsurface tag holder 7 with an RFID tag 4 is inserted into the open section 6 according to the subsurface principle. The subsurface tag holder 7 fills the open section 5 in a bridge-like manner with respect to the hand-held instrument/ring instrument 1 and in a form-adapted manner.

The at least one effector portion 2 has two branches 8 and the at least one gripping portion 3 has two annularly tapering handles 9. The instrument thus preferably forms a pair of scissors (or forceps) of conventional construction. The open section 6 is arranged on a side of the at least one annularly tapering handle 9 facing away from the other annularly tapering handle 9 of the hand-held instrument/ring instrument 1.

Figures 8, 9, 10, 11:
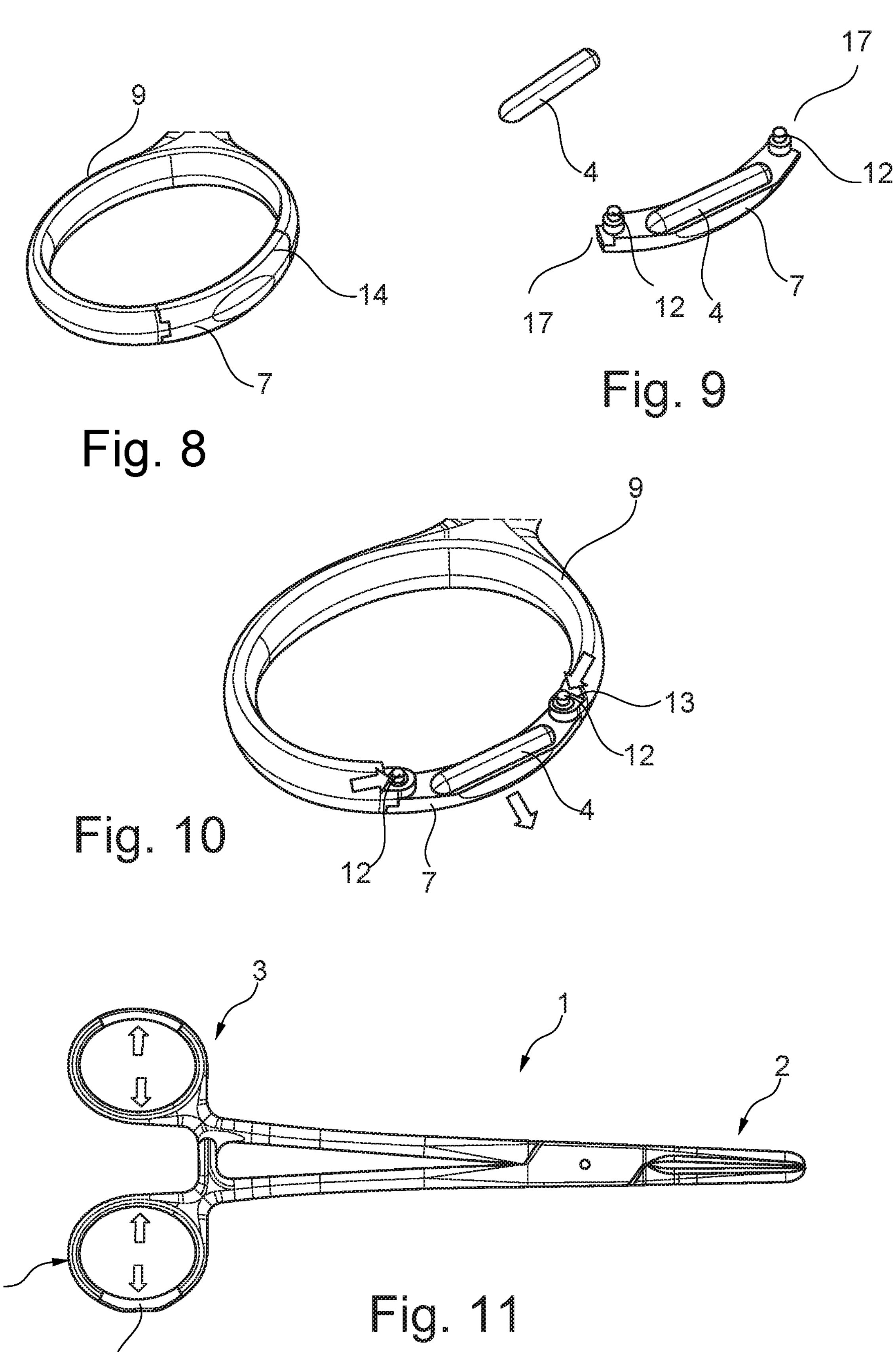
FIG. 8 is a diagram illustrating a handle of the ring instrument in accordance with the second embodiment.
FIG. 9 is a diagram illustrating the subsurface tag holder and the RFID tag in accordance with the second embodiment.
FIG. 10 is a diagram illustrating the application of force to the subsurface tag holder and the RFID tag in accordance with the second embodiment.
FIG. 11 is a diagram illustrating the application of force to the subsurface tag holder 7 of the ring instrument 1 according to the invention, in accordance with the first and second embodiments.

FIG. 8 is a diagram illustrating a handle 9 of the hand-held instrument/ring instrument 1 in accordance with the second embodiment. In FIG. 8, one of the handles 9 of the hand-held instrument/ring instrument 1 according to FIG. 7 is shown enlarged with the inserted subsurface tag holder 7.

The open section 6 is configured in circumferential direction of the annularly tapering handle 9 over the entire thickness height. The open section 6 preferably extends in circumferential direction over a quarter of the entire annularly tapering handle 9.

In FIG. 8, the open section 6 is filled in a bridge-like manner with the subsurface tag holder 7 according to FIG. 9 and a cover 14. The subsurface tag holder 7 is provided to receive the RFID tag 4 therein in a positionally fixed manner according to FIG. 9. The RFID tag 4 is recessed with respect to a surface of the at least one annularly tapering handle 9 toward the interior of the subsurface tag holder 7. The subsurface tag holder 7 is configured such that the RFID tag 4 is exposed to the instrument environment on the inside of the at least one handle 9, as shown in both FIG. 9 and FIG. 10.

FIG. 9 is an illustration of the subsurface tag holder 7 and the RFID tag 4 in accordance with the second embodiment. The subsurface tag holder 7 is configured to be detachably attached to the at least one handle 9 on the upper side near the respective short side 17 via anchor points 12. The upper side of the subsurface tag holder 7 has in each case a protruding anchor point 12, which is configured in each case to insert and/or push in the subsurface tag holder 7 from an underside of the at least one handle 9 in (thickness height direction) toward the upper side (perpendicular to the circumferential direction) into the open section 6, so that each protruding anchor point 12 can be pushed/plugged and/or inserted into in each case a milled recess/receptacle of the at least one handle 9 provided and adapted for this purpose.

The attachable cover 14 is provided for the subsurface tag holder 7 inserted in the at least one handle 9 and can be connected to the subsurface tag holder 7 preferably via adhesive bonding or ultrasonic welding. The cover 14 is adapted to the shape of the annular handle 9 and the subsurface tag holder 7 is inserted in the handle 9. The cover 14 protects the RFID tag 4 inserted in the subsurface tag holder 7 and fills the open section remaining after insertion of the subsurface tag holder 7.

In other words, the anchor points 12 are projections projecting in the upward direction perpendicular to the RFID tag 4 inserted in the subsurface tag holder 7, which are configured in such a way in the vicinity of the short side 17 defined above to be received in annular receptacles of the handle 9 of the medical hand-held instrument 1. The anchor points 12 each have two projection portions, the lower projection portion having a larger diameter than the upper projection portion. The lower projection portion is received by the annular receptacle and the upper projection portion protrudes from the annular receptacle. The upper projection portion is provided to be inserted into the cover 14.

The two annular receptacles are provided on the short side 17 of the open section 6 on the handle 9 of the medical hand-held instrument 1. The annular receptacles are configured approximately halfway up or centered perpendicular to the contact surface or the short side 17 of the handle 9 of the medical hand-held instrument 1. The annular receptacles do not extend over the entire height, but over the entire width of the contact surface or short side 17 of the handle 9 of the medical hand-held instrument 1 and each have a continuous bore in the direction parallel to the contact surface or short side, which are provided to receive the anchor points 12, at least the lower projection portion, of the subsurface tag holder 7.

FIG. 10 shows the insertion of the subsurface tag holder 7 in accordance with the second embodiment. The upper side (the side into which the RFID tag 4 is insertable) of the subsurface tag holder 7 has in each case a protruding anchor point 12, which is configured in each case in order to insert and/or push the subsurface tag holder 7 from an underside of the at least one handle 9 in the direction of the upper side into the open section 6, so that the protruding anchor point 12 can be pushed and/or inserted in each case into a correspondingly provided and adapted annular receptacle/milled recess of the at least one handle 9.

The attachable cover 14 is provided for the subsurface tag holder 7 inserted in the at least one handle 9 and can be connected to the subsurface tag holder preferably via adhesive bonding or ultrasonic welding. The cover 14 is attached onto the subsurface tag holder 7 in the opposite direction to the insertion direction of the subsurface tag holder, so that the subsurface tag holder 7 and the cover 14 approximately continue the shape of the annularly tapering handle 9 of the original shape.

FIG. 11 is a diagram illustrating the application of force to the subsurface tag holder 7 of the ring instrument 1 according to the invention in accordance with the first and second embodiments. According to FIG. 11, the first handle 9 (the upper one in FIG. 11) is configured with the subsurface tag holder 7 in accordance with the first embodiment and the second handle 9 (the lower one in FIG. 11) is configured with the subsurface tag holder 7 in accordance with the second embodiment. This combination of the two subsurface tag holders 7 is merely exemplary. The hand-held instrument 1 may be configured with a subsurface tag holder 7 according to the first embodiment on only one handle 9, or with one subsurface tag holder 7 each according to the first embodiment on both handles 9. Furthermore, the hand-held instrument 1 may be configured with a subsurface tag holder 7 according to the second embodiment on only one handle 9 or with one subsurface tag holder 7 each according to the second embodiment on both handles 9.

FIG. 11 illustrates that a force acts on the subsurface tag holder 7 only when the hand-held instrument/ring instrument 1 is opened, according to the arrows in FIG. 11, which act in the outward direction away from the other handle 9. When the hand-held instrument/ring instrument 1 is closed, no force acts on the subsurface tag holder 7, but only on the side of the handle 9 facing the other handle 9.

Furthermore, the subsurface tag holder 7 (the injection-molded part preferably made of glass or ceramic) with the RFID tag 4 cannot be pushed out even when high force is applied by the user/operator, since the subsurface tag holder 7 in accordance with the first embodiment is held securely in the annular handle 9 of the hand-held instrument 1 by the conical opening and the hemispherical latch 11 and in accordance with the second embodiment by the anchor points 12.

FIG. 10 is an exemplary illustration of the force acting on the subsurface tag holder 7 in accordance with the second embodiment without anchor points 12. In accordance with the second embodiment, the subsurface tag holder 7 tends to be pressed out of the handle 9 when a force is applied to it, possibly through increased force. The optimized geometry of the subsurface tag holder 7 described above allows the force to be absorbed much better and prevents the subsurface tag holder 7 from escaping.

If increased force is applied to the subsurface tag holder 7, the flow of force according to the arrows shown would cause the subsurface tag holder 7 to bend, but would not allow it to detach from the anchor points 12. With increased force applied, this would also be the case, but the choice of material, for example plastic, is important.

Figure 12:
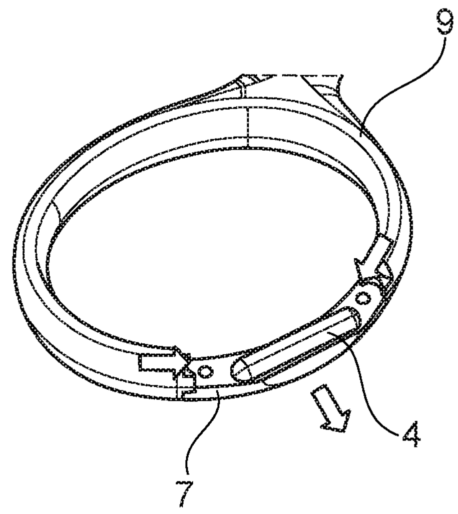
FIG. 12 is an example to illustrate the application of force to the subsurface tag holder.

FIG. 12 is therefore a diagram illustrating the force flow without the advantageous anchor points 12. It does not represent a solution in the sense of the invention. If an increased force is applied, the force flow (according to the arrows shown) would cause the subsurface tag holder 7 to bend and become dislodged from the anchor points 12, possibly shearing off the anchor points 12 and dislodging the subsurface tag holder 7 from the handle 9. This would most likely also break the RFID tag 4.

Figure 13:
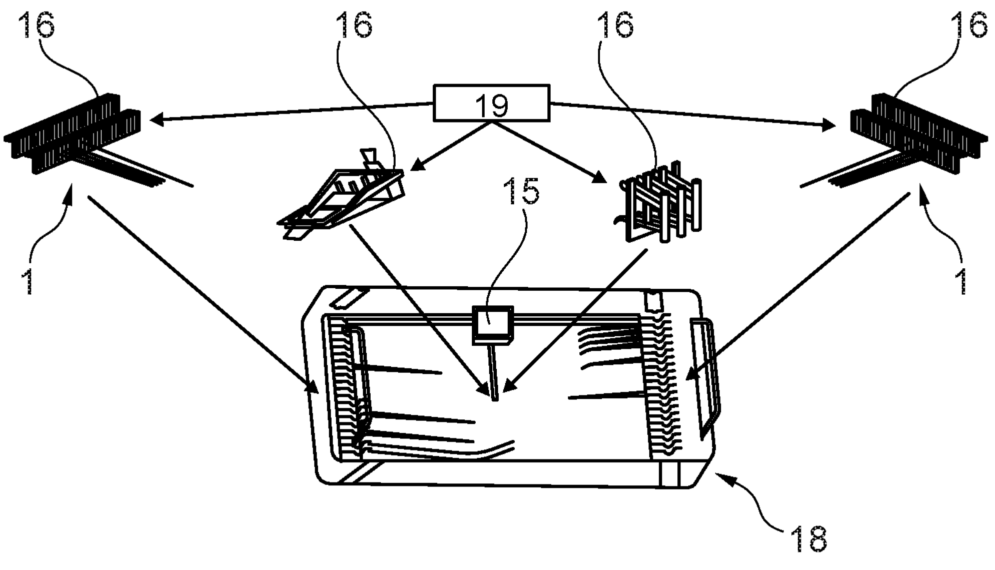
FIG. 13 is a diagram illustrating the system.

FIG. 13 is a diagram illustrating an exemplary system comprising a medical hand-held instrument 1 and a reading device 15 signal-couplable with the RFID tag 4 and configured with or as an instrument holder 16. The instrument holder 16 is provided to hold or temporarily fix the medical hand-held instrument 1 in a predetermined position and/or orientation relative to the reading device 15, in which a signal transmission between RFID tag 4 and reading device 15 is enabled and preferably a plurality of RFID tags 4 are simultaneously and reliably readable.

In other words, a system consisting of a medical hand-held instrument 1 with an instrument body configured as a gripping portion 3 and an effector portion 2, at least one instrument holder 16 and a reading device 15 is shown. The medical hand-held instrument 1, the at least one instrument holder 16 and the reading device 15 are arranged/mounted in a sieve basket/smart tray 18. The reading device 15 is a control module and is connected/in contact with at least one antenna 19.

The positioning of the RFID tag 4 located in the medical hand-held instrument 1 is brought into the closest possible proximity to the reading device 15, allowing the RFID tag 4 to be read. The reading device 15 is connected to at least one antenna 19, which in turn are integrated into the instrument holders 16. Accordingly, the reading device 15 according to this preferred example has a frame according to a sieve basket 18, to which at least one instrument holder 16 is preferably fixed in the form of a clamp or clip, into which the medical hand-held instrument 1 or its instrument body can be clamped/temporarily fixed. Furthermore, FIG. 13 shows the reading device 15, which is located below the medical hand-held instrument 1 when it is inserted into the instrument holder 16. The decisive factor here is that, as a result of its arrangement on the medical instrument according to the invention, the RFID tag 4 can be positioned (as desired) in such a way that it comes to lie exactly above the reading device 15 when the hand-held instrument 1 is inserted in the instrument holder 16, thus minimizing the transmission distance between the RFID tag 4 and the reading device 15.

The positioning of the RFID tag/glass tag 4 is optimal for inserting at least one (handheld) instrument 1 perpendicular into a corresponding instrument holder 16. This ensures the direct proximity of the antenna 19 to the RFID tag 4 and a large number of hand-held instruments 1 and other instruments can be read simultaneously and reliably (100% hit rate).

The invention claimed is:

1. A medical hand-held instrument comprising an instrument body having at least one gripping portion, at least one effector portion, an RFID tag, and a cut-out or open section in the instrument body in a region which is substantially force-free during operative activation of the medical hand-held instrument, wherein in the cut-out or open section, a subsurface tag holder in a form of a bridge or a strip is inserted, which fills the cut-out or open section in a form-adapted manner with respect to the medical hand-held instrument, wherein the subsurface tag holder in the form of a bridge or a strip is configured to connect a first shoulder of the cut-out or open section with a second shoulder of the cut-out or open section, wherein the at least one effector portion has two branches, the at least one gripping portion has a first ring-shaped handle and a second ring-shaped handle, and the cut-out or open section is arranged on a side of the first ring-shaped handle facing away from the second ring-shaped handle;

wherein short sides of the subsurface tag holder each have a protruding latch-behind hemisphere and the short sides are configured at an acute angle to each other in order to insert and/or push the subsurface tag holder into the cut-out or open section, and wherein the subsurface tag holder is pushable or insertable into the cut-out or open section from inside of the first ring-shaped handle in an outward direction, so that the protruding latch-behind hemispheres engage in milled recesses in the first ring-shaped handle.

2. The medical hand-held instrument according to claim 1, wherein the subsurface tag holder is configured to receive the RFID tag in a positionally fixed manner such that the RFID tag is recessed with respect to a surface of the first ring-shaped handle toward an interior of the subsurface tag holder.

3. The medical hand-held instrument according to claim 1, wherein the subsurface tag holder is configured such that the RFID tag is exposed on an inside of the first ring-shaped handle.

4. The medical hand-held instrument according to claim 1, wherein the subsurface tag holder is form-fitted to the first ring-shaped handle via the latch-behind hemispheres on the short side and via anchor points on an upper side.

5. The medical hand-held instrument according to claim 1, further comprising an attachable cover configured to cover the subsurface tag holder inserted into the first ring-shaped handle.

6. The medical hand-held instrument according to claim 5, wherein the attachable cover is connected to the subsurface tag holder via adhesive bonding or ultrasonic welding.

7. The medical hand-held instrument according to claim 1, wherein the subsurface tag holder is a plastic injection-molded part configured to be adapted to an inside of an annular shape of the first ring-shaped handle.

8. A system comprising:

a medical hand-held instrument according claim 1; and a reading device that is signal-coupleable with the RFID tag and configured with or as an instrument holder which is provided and adapted to hold or temporarily fix the medical hand-held instrument in a predetermined position and/or orientation relative to the reading device, in which signal transmission between the RFID tag and the reading device is enabled.

9. The system according to claim 8, wherein the RFID tag comprises a plurality of RFID tags that are simultaneously and securely readable.

10. The medical hand-held instrument according to claim 1, wherein the medical hand-held instrument is one of forceps and scissors.

11. The medical hand-held instrument according to claim 1, wherein the RFID tag is inserted as a glass/ceramic tag in the instrument body.

12. The medical hand-held instrument according to claim 1, wherein the subsurface tag holder is inserted into the cut-out or open section in a force-fitting or a form-fitting manner.

13. The medical hand-held instrument according to claim 1, further comprising an additional cut-out or open section arranged in the second ring-shaped handle, and an additional subsurface tag holder arranged in the additional cut-out or open section, and an additional RFID tag received in the additional subsurface tag holder.

14. The medical hand-held instrument according to claim 13, wherein the additional cut-out or open section is arranged on a side of the second ring-shaped handle facing away from the first ring-shaped handle, and the additional subsurface tag holder is in the form of a bridge or a strip configured to connect a first shoulder of the additional cut-out or open section with a second shoulder of the additional cut-out or open section.

15. The medical hand-held instrument according to claim 1, wherein the cut-out or open section is formed within a continuous ring-shaped surface contour of the first ring-shaped handle.

16. The medical hand-held instrument according to claim 15, wherein the subsurface tag holder or a cover on the subsurface tag holder forms a portion of the continuous ring-shaped surface contour of the first ring-shaped handle when secured to the first ring-shaped handle.

* * * * *